(12) United States Patent
Onishi et al.

(10) Patent No.: US 6,538,160 B2
(45) Date of Patent: Mar. 25, 2003

(54) PROCESS FOR PRODUCING α-AMINOHALOMETHYL KETONE DERIVATIVES

(75) Inventors: Tomoyuki Onishi, Kawasaki (JP); Yasuyuki Otake, Kawasaki (JP); Masakazu Nakazawa, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/730,605

(22) Filed: Dec. 7, 2000

(65) Prior Publication Data

US 2002/0035296 A1 Mar. 21, 2002

(51) Int. Cl.⁷ ................... C07C 221/00; C07C 225/06; C07C 225/10
(52) U.S. Cl. .......................... 564/502; 564/343
(58) Field of Search ................. 564/502, 343

(56) References Cited

FOREIGN PATENT DOCUMENTS

| EP | 816 328 | 1/1998 |
| EP | 834 311 | 4/1998 |
| EP | 878 192 | 11/1998 |

OTHER PUBLICATIONS

Database CAPLUS on STN, Acc. No. 1990:35271, Tezuka et al., 'Generation and reactions of novel copper carbenoids through a stoichiometric reaction of coper metal with gem–dichlorides in DMSO.' J. Org. Chem. (1990), 55(1), pp. 329–333 (abstract).*

Database CASREACT on STN, No. 112:35271, Tezuka et al., 'Generation and reactions of novel copper carbenoids through a stoichiometric reaction of coper metal with gem–dichlorides in DMSO.' J. Org. Chem. (1990), 55(1), pp. 329–333 (reaction 9).*

D.P. Getman, et al. "Discovery of a Novel Class of Potent HIV–1 Protease Inhibitors Containing the (R)–(Hydroxyethyl)urea Isostere", J. Med. Chem., 1993, vol. 36, pp. 288–291.

* cited by examiner

Primary Examiner—Brian J. Davis
(74) Attorney, Agent, or Firm—Oblon, Spivak, McClelland, Maier & Neustadt, P.C.

(57) ABSTRACT

Herein is disclosed a process for producing an α-aminohalomethyl ketone derivative which comprises subjecting to catalytic reduction the corresponding α-aminodihalomethyl ketone derivative, and which process is efficient and suited for industrial production thereof.

15 Claims, No Drawings

PROCESS FOR PRODUCING α-AMINOHALOMETHYL KETONE DERIVATIVES

TECHNICAL FIELD

The present invention relates to a process for producing, from α-aminodihalomethyl ketone derivatives, the corresponding α-aminohalomethyl ketone derivatives; a process for producing the corresponding β-aminoalcohol derivatives by reducing the α-aminohalomethyl ketone derivatives; and a process for producing the corresponding β-aminoepoxide derivatives by treating the β-aminoalcohol derivatives with a base.

BACKGROUND ART

Optically active a-aminohalomethyl ketones are known to be important compounds as an intermediate for the synthesis of an HIV protease inhibitor or the like (Refer to, for example, D. P. Getman, et al., Journal of Medicinal Chemistry, 36, 288(1993); Y. Okada, et al., Chemical and Pharmaceutical Bulletin, 36, 4794(1988); European Patent EP 346867; P. Raddatz, et al., Journal of Medicinal Chemistry, 34, 3267(1991)). There are accordingly demands for the development of a process for producing α-aminohalomethyl ketones which is economical and efficient, and is therefore suited for industrial production.

DISCLOSURE OF THE INVENTION

An object of the present invention is to provide a process for producing α-aminohalomethyl ketones and compounds related thereto which process is economical and efficient and is therefore suited for industrial production.

With a view to attaining the above-described object, the present inventors have carried out an extensive investigation. As a result, it has been found that catalytic reduction of an α-aminodihalomethyl ketone derivative readily yields the intended α-aminohalomethyl ketone derivative. Based on such a finding, the present invention has been completed.

Accordingly, the present invention relates to a process for producing the α-aminohalomethyl ketone derivative represented by the general Formula (2) below which comprises subjecting the corresponding α-aminodihalomethyl ketone derivative represented by the general Formula (1) below to catalytic reduction; a process for producing the β-aminoalcohol derivative which comprises reducing such an α-aminohalomethyl ketone derivative; and a process for producing the β-aminoepoxide derivative which comprises treating such a β-aminoalcohol with a base.

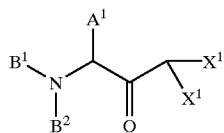

(1)

wherein, $B^1$ and $B^2$ represent, each independently, a hydrogen atom or an amino-protecting group, or $B^1$ and $B^2$ are coupled together to represent an imino type protecting group (with the proviso that $B^1$ and $B^2$ do not represent a hydrogen atom at the same time), $A^1$ represents a $C_{1-10}$ alkyl group, $C_{6-15}$ aryl group or $C_{7-20}$ aralkyl group which groups may be optionally substituted thereon, or a group containing, in the carbon skeleton of such group, a hetero atom, and $X^1$ represents a chlorine atom or a bromine atom.

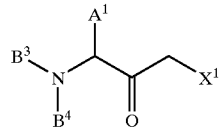

(2)

wherein, $B^3$ and $B^4$ represent, each independently, a hydrogen atom or an amino-protecting group and $A^1$ and $X^1$ have the same meanings as described above, respectively.

The present invention will now be described more specifically hereinafter.

In the general Formulas in the present description, $A^1$ represents a hydrogen atom, a $C_{1-10}$ alkyl group, $C_{6-15}$ aryl group or $C_{7-20}$ aralkyl group, these groups being able to have a substituent thereon, or a group containing, in the carbon skeleton of such group, a hetero atom. Examples of the groups containing a hetero atom in the carbon skeleton include methylthioethyl, t-butylthiomethyl, tritylthiomethyl, (p-methylbenzyl)thiomethyl, (p-methoxybenzyl)thiomethyl, t-butoxymethyl, benzyloxymethyl, t-butoxyethyl, benzyloxyethyl, 4-(t-butoxy)phenylmethyl, 4-benzyloxyphenylmethyl, phenylthiomethyl and the like groups. When the above-exemplified groups have one or more substituents, there are imposed no particular limitations on the substituent(s) insofar as it does or they do not adversely affect the reaction of the present invention. Examples thereof include alkoxyl groups, nitro group, alkyl groups, halogen atoms and the like.

Such a group can be introduced, for example, using an amino acid as a starting material. When $A^1$ represents, e.g., a hydrogen atom, a methyl group, an isopropyl group, a 2-methylpropyl group, a 1-methylpropyl group, a benzyl group and a methylthioethyl group, such groups can be introduced by using, as a starting material, glycine, alanine, valine, leucine, isoleucine, phenylalanine and methionine, respectively.

Alternatively, $A^1$ may be a group introduced by using, as a starting material, an amino acid which has a functional group protected on the side chain of the amino acid. Examples of such amino acid include S-t-butylcysteine, S-tritylcysteine, S-(p-methylbenzyl)cysteine, S-(p-methoxybenzyl)cysteine, O-t-butylserine, O-benzylserine, O-t-butylthreonine, O-benzylthreonine, O-t-butyltyrosine and O-benzyltyrosine.

$A^1$ is not limited to a group introduced from a starting material derived from a natural amino acid, but may be a group introduced from a starting material derived from a non-natural amino acid (for example, a cyclohexylmethyl group, a phenyl group, a phenylthiomethyl group, or the like).

In the general Formulas given in the present description, $X^1$ represents a chlorine atom or a bromine atom.

In the general Formulas given in the present description, $B^1$ and $B^2$ represent, each independently, a hydrogen atom or an amino-protecting group, or $B^1$ and $B^2$ are coupled together to represent an imino type protecting group. $B^1$ and $B^2$, however, do not represent a hydrogen atom at the same time.

There are no particular limitations imposed on the amino-protecting groups. For example, amino-protecting groups as described in "Protecting Groups in Organic Chemistry, 2nd edition" (John Wiley & Sons, Inc. 1991) or the like can be employed. Examples thereof include carbamate type protecting groups such as methoxycarbonyl, ethoxycarbonyl, t-butoxycarbonyl, benzyloxycarbonyl, fluorenylmethoxycarbonyl and the like; acyl type protecting groups such as acetyl, benzoyl and the like; sulfonyl type protecting groups such as methanesulfonyl, benzenesulfonyl, p-toluenesulfonyl and the like; alkyl type protecting groups such as benzyl, p-methoxybenzyl and the like; dialkyl type protecting groups such as dibenzyl and the like; silyl type protecting groups such as trimethylsilyl and the like; and imine type protecting groups such as diphenylmethylene, phenylmethylene, p-methoxyphenylmethylene and the like. Among them, the carbamate type protecting groups are preferred because they can be eliminated easily.

When $B^1$ and $B^2$ are coupled together to represent an imino type protecting group, the α-aminodihalomethyl ketone derivative of the general Formula (1) can, in turn, be represented by the following general Formula (9):

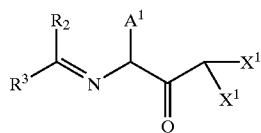

(9)

wherein, $R^2$ and $R^3$ represent, each independently, an aryl group or lower alkyl group which groups may be optionally substituted, or a hydrogen atom. Alternatively, $R^2$ and $R^3$ may be coupled together directly or via a proper group to represent a cyclic structure.

In the general Formulas given in the present description, $B^3$ and $B^4$ represent, each independently, a hydrogen atom or an amino-protecting group. Examples of the amino-protecting group can be the same as those exemplified above.

The α-aminodihalomethyl ketone derivatives represented by the general Formula (1) can be prepared by reacting, as illustrated in the below-described scheme, an α-amino acid ester derivative of the general Formula (10) with a dihalomethyl lithium represented by the general Formula (11). As the dihalomethyl lithium of the general Formula (11), dichloromethyl lithium or dibromomethyl lithium can be used.

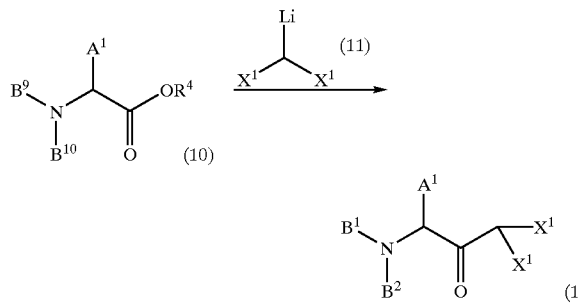

wherein, $B^9$ and $B^{10}$ represent, each independently, a hydrogen atom or an amino-protecting group, or $B^9$ and $B^{10}$ may be coupled together to represent an imino type protecting group with the proviso that $B^9$ and $B^{10}$ do not represent a hydrogen atom at the same time. As the amino-protecting group, those exemplified above can be employed.

In the general Formula (10), $R^4$ represents a lower alkyl or aralkyl group which groups may be optionally substituted. Examples of such lower alkyl or aralkyl group which groups may be optionally substituted include straight- or branched-chain, saturated $C_{1-8}$ alkyl groups which may be optionally substituted and $C_{7-15}$ aralkyl groups which may be optionally substituted. Among them, particularly preferred are straight- or branched-chain, saturated $C_{1-3}$ alkyl groups, such as methyl, ethyl, propyl, isopropyl and a benzyl group which may be optionally substituted. When such groups have one or more substituents, no particular limitations are imposed on the substituent insofar as it does or they do not adversely affect the reaction of the present invention. Examples thereof include alkoxyl groups, nitro group, alkyl groups, halogen atoms and the like.

The α-amino acid ester derivatives represented by the general Formula (10) having the amino group protected can be prepared from an α-amino acid ester and a salt thereof, or an α-amino acid in accordance with the conventional manner.

An N-carbamate-protected α-amino acid ester which is particularly preferred as the α-amino acid ester derivative according to the present invention can be easily synthesized from an α-amino acid ester and a salt thereof by the method ordinarily employed for peptide synthesis.

Furthermore, when the α-amino acid dihalomethyl ketone derivatives of the general Formula (1) above are in the form of those which are protected with an imino group as represented by the general Formula (9), it can be prepared by reacting an α-amino ester derivative of the general Formula (15) with a methyl halolithium, as has been described above. The α-amino acid ester derivatives represented by the general Formula (15) can easily be prepared, as shown in the below-described scheme, from an α-amino acid ester of the general Formula (12) or a salt thereof and an imine compound of the general Formula (13) or an aldehyde or ketone compound of the general Formula (14) in accordance with the known method (for example, A. Dondoni, et al., Synthesis, 1162(1993), M. J. O'Donnell, et al., Journal of Organic Chemistry, 47, 2663(1982)).

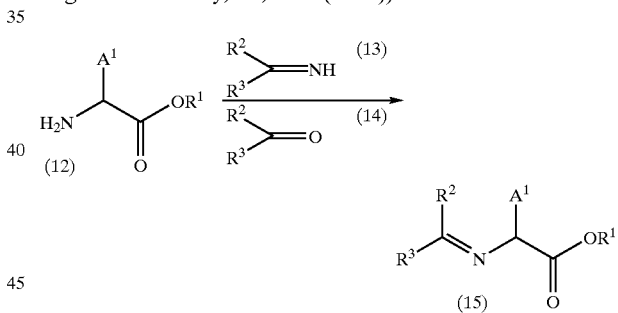

wherein, $R^1$, $R^2$, $R^3$ and $A^1$ have each the same meaning as described above, respectively.

Next will be given the description of a process for preparing the α-aminodihalomethyl ketone derivatives of the general Formula (1) above by reacting an α-amino acid ester derivative of the general Formula (10) above, with a dihalomethyl lithium of the general Formula (11) above.

The dihalomethyl lithium of the general Formula (11) can be prepared, as shown in the below-described scheme, from a dihalomethane of the general Formula (16) and a lithium amide of the general Formula (17).

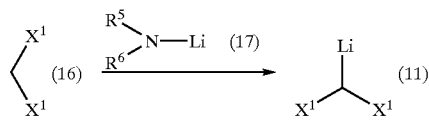

wherein, $X^1$ has the same meaning as described above, and $R^5$ and $R^6$ represent, each independently, an alkyl or trialkylsilyl group, or $R^5$ and $R^6$ may be coupled together directly or via a proper group to represent a cyclic structure.

Examples of the alkyl group include methyl, ethyl, isopropyl, cyclohexyl groups and the like, while those of the trialkylsilyl group include trimethylsilyl and the like. When $R^5$ and $R^6$ are coupled together to represent a cyclic structure, that structure represented by the general Formula (18) can be mentioned as an example.

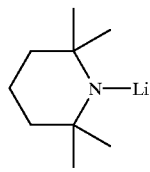

(18)

As the dihalomethane of the general Formula (16) given above, dichloromethane or dibromomethane is usable. Examples of the lithium amide of the general Formula (17) given above include lithium dimethylamide, lithium diethylamide, lithium diisopropylamide, lithium dicyclohexylamide, lithium 2,2,6,6-tetramethylpiperidide, lithium bis(trimethylsilyl)amide, and the like. Among them, particularly preferred is lithium diisopropylamide.

Among dihalomethyl lithiums, dichloromethyl lithium can also be prepared in accordance with the below-described scheme from dichloromethane and a lower alkyl lithium of the general Formula (19) below.

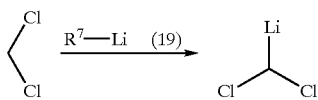

wherein, $R^7$ represents a lower alkyl group.

Examples of the lower alkyl group include straight- or branched-chain, saturated $C_{1-8}$ alkyl groups, with straight-chain, saturated $C_{4-6}$ alkyl groups such as n-butyl, n-pentyl, n-hexyl groups and the like being particularly preferred.

The α-amino acid ester derivative can be reacted with the dihalomethyl lithium, for example, by either one of the following two procedures.

1) A dihalomethyl lithium is prepared in advance by reacting a lithium amide or a lower alkyl lithium with a dihalomethane. To the resultant reaction mixture is then added an α-amino acid ester derivative. The reaction is preferably effected at a temperature ranging from about −120° C. to −50° C.

2) In the presence of an amino acid ester derivative, lithium amide or a lower alkyl lithium is allowed to act on a dihalomethane, whereby the corresponding dihalomethyl lithium is formed in the reaction system. The reaction temperature preferably ranges from about −120° C. to 10° C. Reaction can be effected at a relatively high temperature, for example, −20° C. When the reaction is conducted in this procedure, a carbamate group is preferred as an amino-protecting group.

Preferred examples of the reaction solvent include ether solvents such as tetrahydrofuran, diethyl ether, t-butylmethyl ether and the like. In some cases, such a solvent may be mixed with a nonpolar solvent such as toluene, hexane or the like. This reaction proceeds promptly at a temperature ranging from about −120° C. to 10° C. The reaction is usually completed at −80° C. to −20° C. in 5 to 60 minutes. After completion of the reaction, the reaction mixture may be treated with an aqueous solution of ammonium chloride, a phosphate buffer, dilute hydrochloric acid, dilute sulfuric acid, an aqueous solution of potassium hydrogensulfate or the like.

The α-aminodihalomethyl ketone derivative thus obtained can be purified by procedures known per se in the art such as recrystallization, column chromatography or the like. If there are caused no adverse effects, the derivative may be provided for the subsequent reaction without separation or purification.

The α-aminodihalomethyl ketone derivative (of the general Formula (1)) can be changed into the α-aminohalomethyl ketone derivative (of the general Formula (2)) by a catalytic reduction. Catalytic reduction can be conducted in a manner known per se in the art. There are no particular limitations imposed on the catalysts to be used for reduction insofar as they allow the reaction to proceed smoothly. Examples thereof include palladium, rhodium, ruthenium, platinum, nickel and the like. These catalysts may be held on carbon or the like or may contain water. Among them, palladium is preferred, and it is usually used in the form where it is held on activated charcoal, silica, alumina, barium sulfate, calcium carbonate or the like. Preferred specific examples thereof include palladium-carbon, Lindlar's catalyst (palladium/barium sulfate) and the like. For the catalytic reduction of the α-aminodibromomethyl ketone according the present invention, use of a Lindlar's catalyst is preferred. No particular limitations are imposed on the amount of the catalyst to be used, insofar as it permits completion of the intended reaction. Usually, the catalyst is used in an amount of 0.01 to 10 mole %, preferably 0.1 to 5 mole % relative to the mole number of the α-dihalomethylketone derivative.

As a solvent to be used for reduction, no particular limitations are imposed thereon insofar as it does not adversely affect the reaction and at the same time, permits dissolution of starting materials therein to an extent necessary for the reaction. Examples thereof include water, methanol, ethanol, ethyl acetate and tetrahydrofuran, and a mixture solvent of two or more thereof. To such a solvent, a base such as triethylamine or the like may be added as needed. For example, when a Lindlar's catalyst is employed as the catalyst, it is recommended to neutralize the hydrogen halide byproduced upon reaction with the use of base such as triethylamine. No particular limitations are imposed on the amount of the solvent to be used, insofar as it does not disturb efficient stirring of the reaction mixture. The solvent is usually used in an amount of 1 to 100 times the volume, preferably 5 to 25 times the volume relative to the weight of the α-aminodihalomethyl ketone derivative.

There are no particular limitations imposed on the hydrogen pressure upon reduction, insofar as it permits smooth progress of the reaction. It is preferably 1 to 10 atmospheric pressure.

Concerning the reaction temperature, no particular limitations are imposed thereon, insofar as it permits progress of the resultant reaction and does not permit decomposition of the resultant reaction product. It is usually 0 to 120° C., preferably 20 to 60° C.

After completion of the reaction, the catalyst may be filtered off, and the solvent may be distilled off. The hydrogen halide byproduced upon catalytic reduction can be removed from the reaction system or mixture by adding thereto an amine such as triethylamine, diisopropylethylamine or the like during or after the catalytic reduction whereby the hydrogen halide is converted into the corresponding amine salt, solidifying the resulting amine salt with the use of, or in, a proper solvent such as ethyl acetate, t-butylmethyl ether, toluene and the like, and then filtering off the resulting solid from the reaction system.

The α-aminohalomethyl ketone derivative thus obtained can be purified in a manner known per se in the art such as recrystallization, column chromatography or the like. It may be provided for the subsequent reaction without separation and purification, if there are caused no adverse effects.

With regard to the catalytic reduction step employed in the present invention, a preparation example of an α,α-dialkyl-α-aminochloromethyl ketone by catalytic reduction of an α,α-dialkyl-α-aminodichloromethyl ketone in the racemic form is disclosed in Japanese Patent Application Laid-open (Kokai) No. Hei 10-316563 and Japanese Patent Application Laid-Open (Kokai) No. Hei 10-95757. An actual example of catalytic reduction of an α-monoalkyl-α-aminodichloromethyl ketone is, however, not disclosed anywhere therein.

Furthermore, there have been no reports on the use of an optically active substance, so it has been utterly unknown whether optical activity can be retained or not upon catalytic reduction according to the present invention. Moreover, there have been utterly no reports on a preparation example of α-aminobromomethyl ketone by catalytic reduction of α-aminodibromomethyl ketone.

The compounds according to the present invention include mixtures at any ratio of the two optically active substances including the racemic form, and the two optically active substances. The production process of the present invention can be applied to the synthesis of a compound having optical activity (i.e., an optically active compound) by using an optically active α-amino acid ester obtainable from the esterification of the corresponding optically active amino acid. Optically active amino acids are medically important. I.e., as an α-amino acid ester to be employed as the raw material, that in the L form or D form is preferred, with L-phenylalanine ester useful as the starting material for an HIV protease inhibitor being particularly preferred.

According to the present invention, when an optically active α-amino acid ester derivative is used as the α-amino acid ester derivative, a raw material, the corresponding optical activity can be maintained in the α-aminohalomethyl ketone derivative of the general Formula (2) obtainable by the production process of the present invention. Accordingly, the production process of the present invention is markedly useful as a synthesis process of intermediate compounds for pharmaceuticals.

The following is the reaction scheme when one of the two optically active substances is employed according to the present invention.

wherein, * represents an asymmetric carbon atom, and $B^1$, $B^2$, $B^3$, $B^4$, $A^1$ and $X^1$ have the same meanings as described above, respectively.

Additionally, a production example of an α-aminohalomethyl ketone derivative (S form according to the R/S convention) useful as an intermediate for an HIV protease inhibitor derived from L-phenylalanine is shown below.

wherein, $R^1$ represents a lower alkyl group, benzyl group or fluorenylmethyl group, and $X^1$ has the same meaning as described above.

Examples of the lower alkyl group include straight- or branched-chain, saturated $C_{1-8}$ alkyl groups, out of which the methyl, ethyl and t-butyl groups are preferred.

It is known that the α-aminohalomethyl ketone derivative represented by the general Formula (1) can be changed into the corresponding, but more advanced intermediate through, e.g., the existing two-stage reaction step as shown below (Refer to D. P. Getman, et al., Journal of Medicinal Chemistry, 36, 288(1993)).

Described specifically, the α-aminohalomethyl ketone derivative represented by the general Formula (2) can be changed, by the reduction of the carbonyl group thereof, into the corresponding β-amino alcohol derivative represented by the general Formula (7), and the resulting derivative can be readily epoxidated under alkaline conditions, whereby a β-aminoepoxide derivative represented by the general Formula (8) can be obtained.

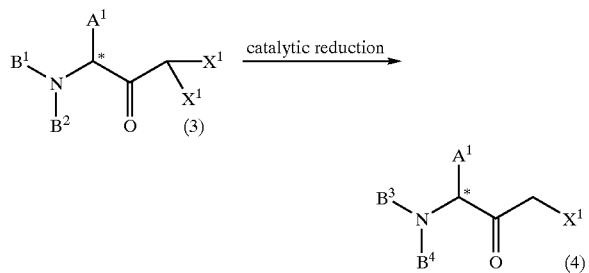

In the Formula (7), $B^5$ and $B^6$ represent, each independently, a hydrogen atom or an amino-protecting group, and $A^1$ and $X^1$ have the same meanings as described above, while in the Formula (8), $B^7$ and $B^8$ represent, each independently, a hydrogen atom or an amino-protecting group, and $A^1$ and $X^1$ have the same meanings as described above.

The production process of the present invention includes, in addition to the case where the protecting group is maintained or not eliminated, the case where after deprotection, reprotection is carried out with the use of the same or another protecting group, the case where after deprotection, re-protection is not conducted, and the case where a protecting group is converted into another protecting group by a reaction.

BEST MODE FOR CARRYING OUT THE INVENTION

The present invention will be further described in detail with reference to Referential Examples and Examples. The present invention is of course not limited by the Examples.

Referential Example 1

Production process of N-tert-butoxycarbonyl-L-phenylalanine methyl ester

To a mixed solvent of methanol (50 ml) and water (100 ml) were added L-phenylalanine methyl ester hydrochloride (21.6 g), sodium carbonate (11.64 g), and a solution of di-tert-butoxydicarbonate (21.8 g) in methanol (100 ml). The resulting mixture was heated to 40° C., followed by stirring for 6 hours. The reaction mixture was concentrated to remove the methanol. The concentrate was extracted by adding ethyl acetate and water. The resulting ethyl acetate layer was washed with 0.1 N hydrochloric acid, water, an aqueous sodium hydrogencarbonate solution and a saturated solution of sodium chloride. The ethyl acetate layer after washed was dried over anhydrous magnesium sulfate. The magnesium sulfate was filtered off. The solvent was distilled off under reduced pressure to give the target N-tert-butoxycarbonyl-L-phenylalanine methyl ester (26.4 g) in a yield of 95%.

$^1$H-NMR (CDCl$_3$, 300 MHz) δ ppm: 1.39 (s, 9H), 2.98–3.16 (m, 2H), 3.69 (s, 3H), 4.54–4.65 (m, 1H), 4.93–5.03 (bd, 1H), 7.08–7.32 (m, 5H)

Referential Example 2

Production process of (3S)-3-tert-butoxycarbonylamino-1,1-dichloro-4-phenyl-2-butanone After cooling dehydrated tetrahydrofuran (15 ml) to −78° C., a 2M solution (5.75 ml) of lithium diisopropylamide in heptane, tetrahydrofuran and ethyl benzene was added thereto. Then, a solution of methylene chloride (0.74 ml) in dehydrated tetrahydrofuran (5 ml) was added thereto. The mixture was stirred for 10 minutes. A solution of N-tert-butoxycarbonyl-L-phenylalanine methyl ester (1.4 g) in dehydrated tetrahydrofuran (7 ml) was then added thereto, followed by stirring for 1 hour. The reaction was terminated by the addition of 1N hydrochloric acid (25 ml) to the reaction mixture. After heating to room temperature, the reaction mixture was added with ethyl acetate and water for extracting. The ethyl acetate solution thus obtained was analyzed by HPLC. As a result, it was confirmed that the target (3S)-3-tert-butoxycarbonylamino-1,1-dichloro-4-phenyl-2-butanone (1.31 g) had been formed in a yield of 79%.

As a result of analysis of the (3S)-3-tert-butoxycarbonylamino-1,1-dichloro-4-phenyl-2-butanone existent in the ethyl acetate solution by HPLC using an optically active column, it was confirmed that the optical purity thereof was greater than 99.5% e.e. The ethyl acetate solution was then dried over anhydrous magnesium sulfate. The magnesium sulfate was filtered off. From the filtrate, the solvent was distilled off under reduced pressure. By the addition of ethyl acetate, the resulting residue was made into a slurry. The crystals were then separated from the slurry and dried, whereby the target (3S)-3-tert-butoxycarbonylamino-1,1-dichloro-4-phenyl-2-butanone (1.12 g) was obtained in a yield of 67%.

As a result of analysis of the crystals thus separated of the (3S)-3-tert-butoxycarbonylamino-1,1-dichloro-4-phenyl-2-butanone by HPLC using an optically active column, it was confirmed that the optical purity thereof was greater than 99.5% e.e.

$^1$H-NMR (CDCl$_3$, 300 MHz) δ ppm: 1.40 (s, 9H), 3.01 (dd, J=7.9, 13.8 Hz, 1H), 3.22 (dd, J=5.7, 13.8 Hz, 1H), 4.62–5.00 (m, 2H), 6.08 (s, 1H), 7.17–7.22 (m, 2H), 7.22–7.36 (m, 3H). $[α]_D^{20}$=−52.7° (c=2.25, CH$_2$Cl$_2$).

EXAMPLE 1

Production process of (3S)-3-tert-butoxycarbonylamino-1-chloro-4-phenyl-2-butanone To (3S)-3-tert-butoxycarbonylamino-1,1-dichloro-4-phenyl-2-butanone (67.1 mg) were added methanol (2.0 ml) and 10% palladium-carbon (7.0 mg). After replacement with hydrogen gas was carried out, the mixture was stirred for 30 minutes. The reaction mixture was filtered. Triethylamine (0.0273 ml) was added to the filtrate, followed by concentrating to remove the methanol. Ethyl acetate was then added to the residue. From the mixture, the resulting triethylammonium chloride was filtered off. The filtrate was concentrated to remove the ethyl acetate. Crystallization from isopropanol gave (3S)-tert-butoxycarbonylamino-1-chloro-4-phenyl-2-butanone (39.7 mg) in a yield of 66%.

As the results of analysis of the reaction mixture and the crystals thus obtained, by HPLC using an optically active column, it was confirmed that the optical purity thereof was greater than 99.5% e.e., and that a series of reactions proceeded while maintaining the optical purity of the L-phenylalanine methyl ester hydrochloride.

$^1$H-NMR (CDCl$_3$, 300 MHz) δ ppm: 1.41 (s, 9H), 3.00 (dd, J=6.9, 13.8 Hz), 3.08 (dd, J=6.9, 13.8 Hz, 1H), 3.98 (d, J=16.2 Hz, 1H), 4.17 (d, J=16.2 Hz, 1H), 4.68 (q, J=6.9 Hz, 1H), 5.02 (bd, J=6.9 Hz, 1H), 7.16 (m, 2H), 7.26–7.36 (m, 3H).

Mass spectrum m/e: 296.1 (M$^-$H$^-$). $[α]_D^{25}$=−55.7° (c=1, EtOH).

EXAMPLE 2

Production process of (3S)-3-tert-butoxycarbonylamino-1-chloro-4-phenyl-2-butanone To (3S)-tert-butoxycarbonylamino-1,1-dichloro-4-phenyl-2-butanone (63.1 mg) were added methanol (1.9 ml), triethylamine (0.0265 ml) and 5% Lindlar catalyst (palladium/barium sulfate) (14.2 mg). After replacement with hydrogen gas was carried out, the mixture was stirred for 3 hours. The reaction mixture was filtered, followed by concentrating to remove the methanol. Ethyl acetate was then added to the residue. From the mixture, the resulting triethylammonium chloride was filtered off. The filtrate was concentrated to remove the ethyl acetate. Crystallization from isopropanol gave (3S)-tert-butoxycarbonylamino-1-chloro-4-phenyl-2-butanone (36.2 mg) in a yield of 64%.

As the results of analysis of the reaction mixture and the crystals thus obtained, by HPLC using an optically active column, it was confirmed that the optical purity thereof was greater than 99.5% e.e., and that a series of reactions proceeded while maintaining the optical purity of the L-phenylalanine methyl ester hydrochloride.

Referential Example 3

Production process of (3S)-1,1-dibromo-3-tert-butoxycarbonylamino-4-phenyl-2-butanone After cooling dehydrated tetrahydrofuran (15 ml) to −78° C., a 2M solution (6.25 ml) of lithium diisopropylamide in heptane, tetrahydrofuran and ethyl benzene was added thereto. Then, a solution of dibromomethane (0.88 ml) in dehydrated tetrahydrofuran (5 ml) was added. The mixture was stirred for 10 minutes. A solution of N-tert-butoxycarbonyl-L-phenylalanine methyl ester (1.4 g) in dehydrated tetrahydrofuran (7 ml) was added thereto, followed by stirring for 1 hour. The reaction was terminated by the addition of 1N hydrochloric acid (25 ml) to the reaction mixture. After heating to room temperature, the reaction mixture was added with ethyl acetate for extracting. The ethyl acetate solution thus obtained was analyzed by HPLC. As a result, it was confirmed that the target (3S)-1,1-dibromo-3-tert-butoxycarbonylamino-4-phenyl-2-butanone (1.14 g) had been formed in a yield of 53%. The ethyl acetate solution was then dried over anhydrous magnesium sulfate. The magnesium sulfate was filtered off. From the filtrate, the solvent was distilled off under reduced pressure. By the addition of ethyl acetate, the resulting residue was made into a slurry. The crystals were then separated from the slurry and dried, whereby the target (3S)-1,1-dibromo-3-tert-butoxycarbonylamino-4-phenyl-2-butanone (1.04 g) was obtained in a yield of 46%.

$^1$H-NMR (CDCl$_3$, 300 MHz) δ ppm: 1.41 (s, 9H), 3.04 (dd, J=7.3, 13.8 Hz, 1H), 3.20 (dd, J=6.2, 13.8 Hz, 1H), 4.64–5.05 (m, 2H), 6.00 (s, 1H), 7.17–7.37 (m, 5). $[\alpha]_D^{20}$=−40.6° (c=2.0, CH$_2$Cl$_2$).

EXAMPLE 3

Production process of (3S)-tert-butoxycarbonylamino-1-bromo-4-phenyl-2-butanone

To (3S)-3-tert-butoxycarbonylamino-1,1-dibromo-4-phenyl-2-butanone (31.5 mg) were added methanol (0.75 ml), triethylamine (0.0105 ml) and 5% Lindlar catalyst (palladium/barium sulfate) (7.2 mg). After replacement with hydrogen gas was carried out, the mixture was stirred for 2.5 hours. The reaction mixture was filtered, followed by concentrating to remove the methanol. Ethyl acetate was then added to the residue. From the mixture, the resulting triethylammonium chloride was filtered off. The filtrate was concentrated to remove the ethyl acetate. Crystallization from isopropanol gave (3S)-tert-butoxycarbonylamino-1-bromo-4-phenyl-2-butanone (16.7 mg) in a yield of 65%.

$^1$H-NMR (CDCl$_3$, 300 MHz) δ ppm: 1.41 (s, 9H), 2.98–3.19 (m, 2H), 3.84 (d, J=13.8 Hz, 1H), 3.96 (d, J=13.8 Hz, 1H), 4.72 (dd, J=6.9, 6.9 Hz, 1H), 5.05 (bd, J=6.9 Hz, 1H), 7.13–7.38 (m, 5H). $[\alpha]_D^{20}$=−49.6° (c=1.1, MeOH).

Industrial Applicability

According to the present invention, α-aminohalomethyl ketone derivatives can be produced economically and efficiently, and because the initial optical activity of the relevant compounds can be maintained, the production process of the present invention is particularly useful for the production of pharmaceutical intermediates.

What is claimed is:

1. A process for producing an α-aminohalomethyl ketone compound represented by the general Formula (2) below which comprises subjecting to catalytic reduction a corresponding α-aminodihalomethyl ketone compound by the general Formula (I)

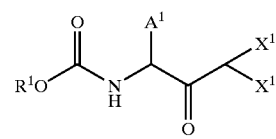

(1)

wherein, R$^1$ represents a lower alkyl group, benzyl group or a phenyl group, A$^1$ represents a C$_{1-10}$ alkyl group, C$_{6-15}$ aryl group or C$_{7-20}$ aralkyl group which groups may be optionally substituted thereon, or a group containing, in the carbon skeleton of such group, a hetero atom, and X$^1$ represents a chlorine atom or a bromine atom

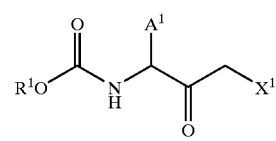

(2)

wherein, R$^1$, A$^1$ and X$^1$ represent the same meanings as described above, respectively.

2. A process for producing an α-aminohalomethyl ketone compound represented by the general Formula (6) below which comprises subjecting to catalytic reduction a corresponding α-aminodihalomethyl ketone compound represented by the general Formula (5) below

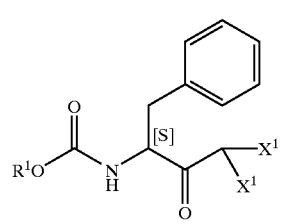

(5)

wherein, R$^1$ represents a lower alkyl group, benzyl group or a phenyl group, and X$^1$ represents a chlorine atom or a bromine atom

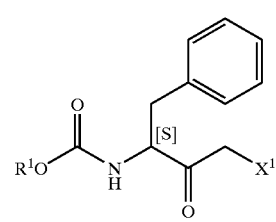

(6)

wherein, R$^1$ and X$^1$ represent the same meanings as described above, respectively.

3. A process for producing a α-aminohalomethyl compound represented by the general Formula (7)

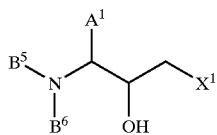

(7)

wherein $B^5$ and $B^6$ represent, each independently, a hydrogen atom or an amino-protecting group, $A^1$ represents a $C_{1-10}$ alkyl group, $C_{6-15}$ aryl group or $C_{7-20}$ aralkyl group which groups may be optionally substituted thereon, or a group containing, in the carbon skeleton of such group, a hetero atom, and $X^1$ represents a chlorine atom or a bromine atom, said process comprising reducing a corresponding α-aminohalomethyl ketone compound represented by the general formula (2)

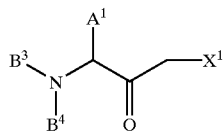

(2)

wherein $B^3$ and $B^4$ represent, each independently, a hydrogen atom or an amino-protecting group, and $A^1$ and $X^1$ have the same meanings as described above, respectively, wherein said compound of Formula (2) is prepared by subjecting to catalytic reduction a corresponding α-aminodihalomethyl ketone compound represented by the general Formula (1)

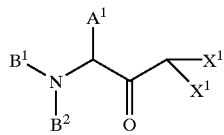

(1)

wherein $B^1$ and $B^2$ represent, each independently, a hydrogen atom or an amino-protecting group, or $B^1$ and $B^2$ are coupled together to represent an imino type protecting group (with the proviso the $B^1$ and $B^2$ do not represent a hydrogen atom at the same time), $A^1$ represents a $C_{1-10}$ alkyl group, $C_{6-15}$ aryl group or $C_{7-20}$ aralkyl group which groups may be optionally substituted thereon, or a group containing, in the carbon skeleton of such group, a hetero atom, and $X^1$ represents a chlorine atom or a bromine atom.

4. A process for producing a β-aminoepoxide compound represented by the general Formula (8) below which comprises treating, with a base, a corresponding β-aminoalcohol compound represented by the general Formula (7) which has been produced by the process of claim 3

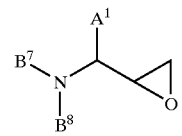

(8)

wherein, $B^7$ and $B^8$ represent, each independently, a hydrogen atom or an amino-protecting group, and $A^1$ has the same meaning as described above.

5. The process of claim 1, wherein said catalytic reduction is carried out using a catalyst selected from the group consisting of palladium, rhodium, ruthenium, platinum, and nickel.

6. The process of claim 1, wherein said catalytic reduction is carried out using a catalyst which is palladium.

7. The process of claim 2, wherein said catalytic reduction is carried out using a catalyst selected from the group consisting of palladium, rhodium, ruthenium, platinum, and nickel.

8. The process of claim 2, wherein said catalytic reduction is carried out using a catalyst which is palladium.

9. The process of claim 2, wherein said catalytic reduction is carried out with 0.01 to 10 mole % of catalyst per mole of said α-aminodihalomethyl ketone.

10. The process of claim 2, wherein said catalytic reduction is carried out with 0.1 to 5 mole % of catalyst per mole of said α-aminodihalomethyl ketone.

11. The process of claim 2, wherein said catalytic reduction is carried out with a hydrogen pressure of 1 to 10 atmospheres.

12. The process of claim 2, wherein said catalytic reduction is carried out at a temperature of 0° C. to 120° C.

13. The process of claim 2, wherein said catalytic reduction is carried out at a temperature of 20° C. to 60° C.

14. The process of claim 4, wherein $A^1$ is a benzyl group; $B^4$ and $B^6$ are both hydrogen; and $B^3$ and $B^5$ are both a group of the formula $R^1OC(=O)$, wherein $R^1$ is selected from the group consisting of lower alkyl, benzyl, and phenyl.

15. The process of claim 4, wherein $A^1$ is a benzyl group; $B^4$ and $B^8$ are both hydrogen; and $B^3$ and $B^7$ are both a group of the formula $R^1OC(=O)$, wherein $R^1$ is selected from the group consisting of lower alkyl, benzyl, and phenyl.

* * * * *